United States Patent [19]

McAleer et al.

[11] 3,933,585

[45] Jan. 20, 1976

[54] PROCESS FOR PRODUCTION OF VACCINES

[75] Inventors: William J. McAleer, Ambler, Pa.; Raymond E. Spier, Guildford, Surrey, England; Kenneth L. Posch, Lansdale, Pa.

[73] Assignee: Merck & Co., Inc., Rahway, N.J.

[22] Filed: May 31, 1974

[21] Appl. No.: 475,063

Related U.S. Application Data

[63] Continuation-in-part of Ser. No. 262,825, June 14, 1972, abandoned.

[52] U.S. Cl. .................. 195/1.1; 195/1.7; 195/1.8; 424/89
[51] Int. Cl.².. A61K 39/12; C12B 1/00; C12K 7/00
[58] Field of Search ................ 424/89; 195/1.7, 1.1

[56] References Cited
OTHER PUBLICATIONS

Litwin, *Process Chemistry*, pp. 15–17, July 1971.
Molin et al., Progr. Immunobiol. Standard, Vol. 3, pp. 106–110, 1969.
Technical Specification for FL203 Diploid Cell Cultivation Apparatus, published by Biotec. Inc., Rockville, Md., 2 pp.

*Primary Examiner*—Sam Rosen

[57] ABSTRACT

A multiplate propagator for producing cells and vaccines having critical geometric properties such as ratio of plate diameter to internal tank diameter results in significantly increased yields at substantially reduced costs.

5 Claims, 2 Drawing Figures

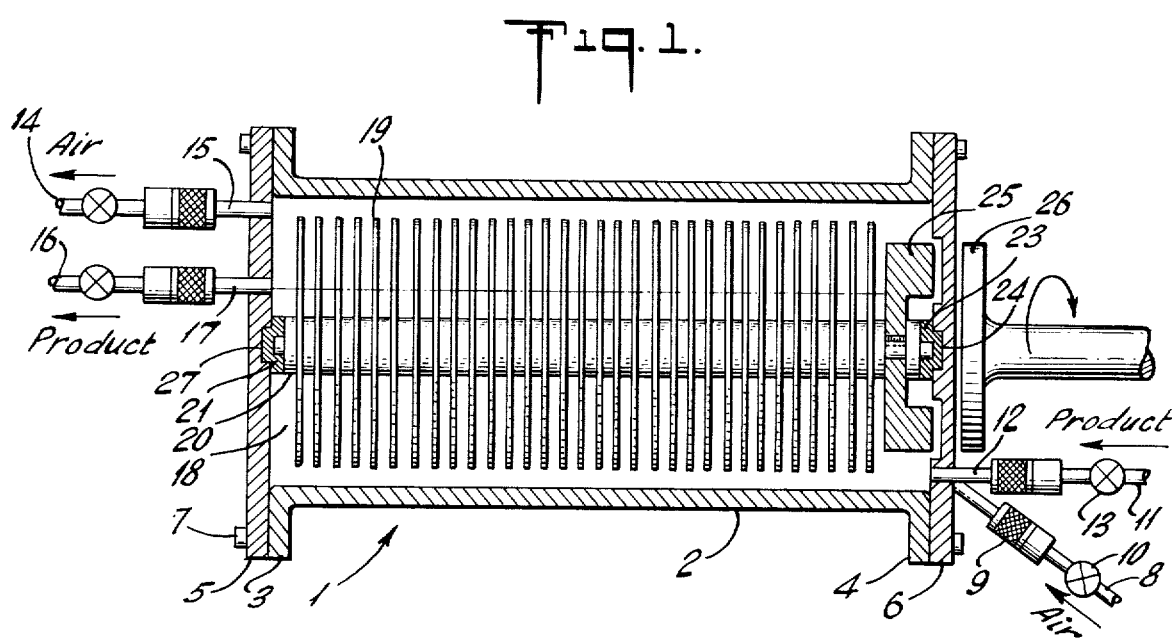

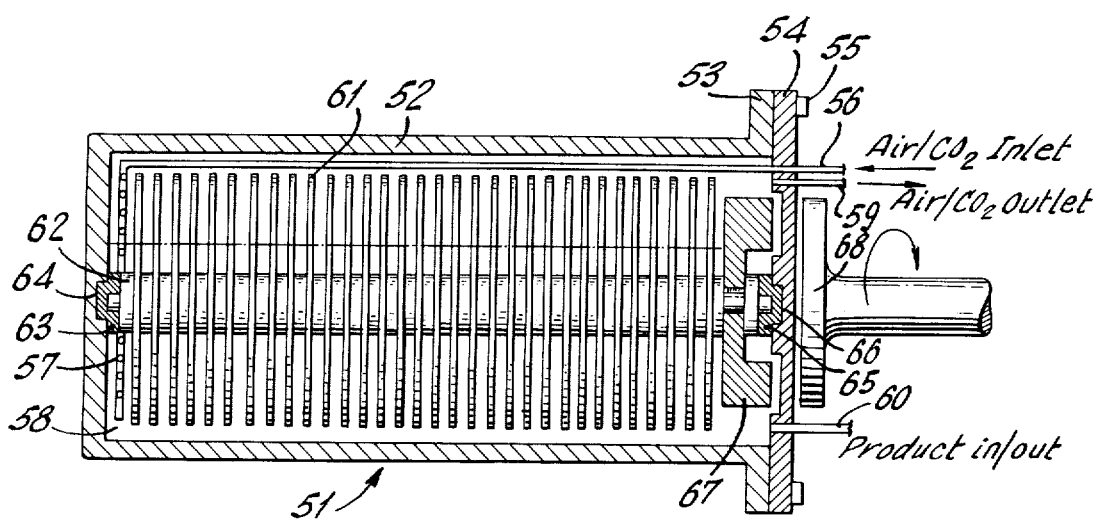

PROCESS FOR PRODUCTION OF VACCINES

This application is a continuation-in-part of our copending application Ser. No. 262,825, filed June 14, 1972, now abandoned.

This invention relates to a process for producing cells and vaccines.

More particularly, this invention relates to a process for producing cells and vaccines which utilizes a multi-plate propagator having critical geometric properties such as the plate diameter to internal tank diameter ratio, in order to produce the cells and vaccines in significantly increased yields and at substantially reduced costs as compared to presently utilized procedures.

Human and animal vaccines have been commercially produced by growing the desired virus in primary cells which must be grown on surfaces. Commercial processes were initially developed in Brockway bottles and, as production techniques evolved, the Brockway bottles were replaced by roller bottles. More recently, mass culture systems have been developed, including those which utilize a series of concentric rings or tanks having a plurality of stacked plates. The most recent mass culture system which has been developed is the multiplate machine produced by Biotic A. B. of Sweden which contains a series of titanium discs or plates which are mounted on a rotatable shaft in a cylindrical glass vessel. The vessel is capable of being placed in the upright position, in which the plating surface of the discs is in a horizontal plane in order to permit the cells to settle onto the plating surface of the discs. The device is then placed on its side so that the plated cells are rotated through the growth medium in the vessel until cell sheet formation occurs, the virus seed is then added, the unit is again rotated and the vaccine is harvested.

As the state of the art evolved, the primary objective was to increase the yield and reduce production costs by increasing the surface area or cell plating area to volume of medium ratio in order to obtain the highest yield of cells and vaccine in the smallest volume. For example, a surface area to volume ratio on a cm.$^2$/ml. basis of 3.0 cm.$^2$/ml. had been achieved in the Biotec apparatus. We have unexpectedly discovered that significant increases in the yield of cells and vaccines are obtained by using a device which has a surface area to volume ratio of from about 1.7 cm.$^2$/ml. to about 2.2 cm.$^2$/ml. and preferably a value of 1.9 cm.$^2$/ml.

We have also discovered that yields of cells and vaccines can be obtained which are significantly greater than the yields of cells and vaccines which are produced using any of the aforementioned devices by utilizing multi-plate propagators which have a critical plate diameter to internal tank diameter ratio, or which have a critical distance between the periphery of the plates and the inner wall of the tank. This diameter ratio may be from about 0.80 to about 0.90, preferably from about 0.82 to about 0.84 as compared to 0.96 in the Biotec unit. The critical distance between the periphery of the plate and the inner wall of the tank is from about one-half inch to about three-quarter inch and preferably a value of five-eighths inch as opposed to one-eighth inch in the Biotec unit.

The use of a device which contains the critical surface area to volume ratio, or critical plate diameter to internal tank diameter ratio, or critical distance between the periphery of the plates and the inner wall of the tank leads to significant increases in the yield of cells and vaccines when compared with conventional cell and vaccine propagation systems including the multiplate propagator manufactured by Biotec.

An advantage of the present invention is the production of cells and vaccines in very high yields, and at substantially reduced costs as compared to the procedure utilized in the prior art.

A further advantage of the present invention is that the yield of cells is greatly increased on all plating surfaces.

A still further advantage of the present invention is that equivalent amounts of cells and vaccines may be produced while substantially reducing the number of production units, thereby reducing handling costs and the risk of contamination.

The process of the present invention may be used to produce viral vaccines such as mumps, measles, rubella, Marek's, influenza, parainfluenza, varicella, and respiratory syncytia and cells such as WI-38, chick embryo and duck embryo cells, Standard cells, sera, and media may be used to charge the propagator. For example, primary cells such as chick embryo fibroblasts, green monkey kidney, bovine kidney, dog kidney cells or diploid cells such as WI-38 may be utilized as may standard sera such as fetal calf, calf, bovine, G-G-free new born calf, $\alpha$-gamma calf or $\alpha$-gamma bovine and standard media such as Eagles Basel Medium, Medium 199, Medium EBME and Eagle's Minimum Essential Medium (EMEM).

The process of the present invention will be better understood by an examination of the accompanying drawing in which:

FIG. 1 is a sectional view of a multiplate propagator which is exemplary of those which can be utilized in accordance with the process of this invention; and FIG. 2 is a sectional view of another multiplate propagator which is exemplary of those which can be utilized in accordance with the process of this invention.

Referring to FIG. 1, there is disclosed a propagator 1 which comprises a cylindrical stainless steel tank 2 having flanges 3 and 4 at each end thereof. Top and bottom plates 5 and 6 are sealed to flanges 3 and 4 by clamps 7. An air-carbon dioxide mixture is pumped into the tank 2 from a reservoir (not shown) through a line 8 which is connected to the tank by a coupling device 9 in plate 6. A valve 10 is used to control the rate of flow of this mixture to the tank. Additional medium, serum and other nutrients may be supplied to the tank through line 11 which is connected to the tank by coupling device 12. A valve 13 is used to control the rate of flow of nutrients to the tank. Outlet line 14 is connected to the tank by coupling device 15 which is in the upper portion of plate 5 in order to remove air from the tank so that the air pressure inside the tank does not build up to an unsatisfactory level. A further line 16 is connected to the tank 1 by coupling device 17 which is located slightly above the center of plate 5 in order to permit fluids to be withdrawn from the tank, thereby preventing the level of fluid or medium 18 in the tank from rising above the desired level. It is necessary to control the level of the medium in order to insure the proper aeration of the plates 19 as they rotate through the medium. The plates 19 are mounted on a bar 20, which supports the plates 19 in a separated state due to the presence of cylindrical spacers between each plate. One end of the bar 20 is rotatably supported by a bearing 21 which is mounted in recess 27 in end plate 5. The other end of the bar 20 is also rotatably supported by a bearing 23 which is mounted in a recess 24 in end plate 6. A magnetic couple 25 which is fixedly mounted on bar 20 is engaged by magnetic drive means 26 to rotate the plates 19 through the medium 18 during the cell growth and virus infection stages of operation.

Similarly in FIG. 2, there is disclosed a propagator 51 which comprises a cylindrical stainless steel vessel 52 having a flange 53 at one end thereof. Plate 54 is sealed to the flange 53 by clamps 55. An air-carbon dioxide mixture is pumped into the vessel 52 from a reservoir (not shown) through a line 56 which extends along the length of the wall of the vessel 52 to the back of the vessel 52 where a portion of the line 56 extends along the back of the vessel. This portion of the line 56 has openings 57 which permit the egress of the air-carbon dioxide mixture. An outlet line 59 is also used to keep the air pressure within the vessel at a relatively constant level. Another line 60 is used to supply medium, serum and other nutrients and to withdraw the expended medium and product. The fluid 58 is maintained at a level of slightly more than half of the maximum volume to insure the proper aeration of the plates 61 as they rotate through the medium. The plates 61 are mounted on a bar 62, which supports the plates 54 in a separated state due to the presence of cylindrical spacers between each plate. One end of the bar 62 is rotatably supported by a bearing 63 which is mounted in recess 64 in the bottom of the vessel 52. The other end of the bar 62 is also rotatably supported by a bearing 65 which is mounted in a recess 66 in plate 54. A magnetic couple 67 which is fixedly mounted on bar 62 is engaged by a driven magnet 68 to rotate the plates 61 through the medium 58 during the cell growth and virus infection stages of the production cycle.

The process of the present invention will be better understood by reference to the following examples:

EXAMPLE 1

A rotating titanium disc propagator having a stack of 50 discs, each having a plate diameter of 6 inches, an internal tank diameter of 7-¼ inches, a distance of five-eighths inch between the edge of the plates and the tank wall and a plate diameter to internal tank diameter ratio of 0.83 is charged with a mixture of 1.5 billion trypsinized chick embryo cells and Medium 199 containing 45 ml. 2.8% $NaHCO_3$/L and 10% fetal calf serum. The propagator is held in the vertical position at a temperature of 37°C. and plating is effected. The propagator is then positioned so that the plane of the discs is in the vertical axis and a portion of the medium and serum is discharged until the unit is half full or slightly more than half full. The discs are then rotated at a speed of 1 revolution/5 minutes and air or a mixture of 95% air and 5% $CO_2$ is passed through the unit at a rate of 100 cc/minute until the cell growth cycle has been completed at which time the spent medium and serum is discharged from the propagator and the propagator is washed with Hank's solution and charged with fresh Medium 199, containing 60 ml. 2.8% $NaHCO_3$/L, and 25% SPGA containing a suspension of mumps virus derived from 1 ml. of a suspension which has a $-\log_{10}$ $TCID_{50}$/0.1 ml. of 3.6. The unit is again rotated at a speed of 1 revolution/5 minutes until there is no further increase in the concentration of virus in the supernatant fluids at which time the vaccine harvesting operation begins.

When the titer of mumps vaccine prepared according to the procedure set forth in this example is compared to that of the mumps vaccine produced by conventional procedures a greater than ten fold increase in titer is observed. This leads to substantially increased yields of vaccine.

EXAMPLE 2

A rotating disc propagator having a stack of 50 discs, each having a plate diameter of 6 inches, an internal tank diameter of 7 ¼ inches, a distance of five-eighths inch between the edge of the plates and the tank wall, a plate diameter to internal tank diameter ratio of 0.80, and a surface area to volume ratio of 1.9 $cm.^2$/ml. is charged with a mixture of 1.5 billion trypsinized chick embryo cells and Medium 199 containing 45 ml. 2.8% $NaHCO_3$/L and 10% fetal calf serum. The propagator is held in the vertical position at a temperature of 37°C. and plating is effected. After 3 hours the fluid in the propagator is discharged and a further 1.5 billion trypsinized chick embryo cells are added to it and, after mixing, the fresh suspension is transferred back into the propagator which is held in the opposite vertical position to the first plating at a temperature of 37°C. After plating has been completed the propagator is then positioned so that the plane of the discs is in the vertical axis and a portion of the medium and serum is discharged until the unit is about half full. The discs are then rotated at a speed of 1 revolution/5 minutes and a mixture of 95% air and 5% $CO_2$ is passed through the unit at a rate of 100 cc/min. until the cell growth cycle is completed at which time the spent medium and serum is discharged from the propagator. The propagator is then refed with fresh Medium 199 containing 60 ml. 2.8% $NaHCO_3$/L, and 2% G-G-free newborn calf serum and 11 ml. of measles virus suspension which has a $-\log_{10}$ $TCID_{50}$/0.1 ml. of 3.3 and rotated until the infection process is complete at which time the spent fluids are discharged and the contents of the propagator are washed with Hank's solution. The propagator is then recharged with fresh Medium 199 and 60 ml. 2.8% $NaHCO_3$/L 10% SPGA. When the vaccine has reached the desired concentration, the vaccine harvesting operation begins.

When the titer of measles vaccine prepared according to the procedure set forth in this example is compared to that of measles vaccine produced by conventional procedures, a significant increase in titer is observed. This leads to substantially increased yields of vaccine.

EXAMPLE 3

A rotating disc propagator having a stack of 50 discs, each having a plate diameter of 5.4 inches, an internal tank diameter of 6 inches, a distance of 0.3 inch between the edge of the plates and the tank wall and a plate diameter to internal tank diameter ratio of 0.90 is charged with a mixture of 1.5 billion trypsinized duck embryo cells and Medium 199 containing 45 ml. 2.8% $NaHCO_3$/L and 10% fetal calf serum. The propagator is held in the vertical position at a temperature of 37°C. and plating is effected. After 3 hours the fluid in the propagator is then discharged and a further 1.5 billion trypsinized duck embryo cells are added to it and after mixing the fresh suspension is transferred back into the propagator which is held in the opposite vertical position to the first plating at a temperature of 37°C. After plating has been completed the propagator is then positioned so that the plane of the discs is in the vertical axis and a portion of the medium and serum is discharged until the unit is about half full. The discs are then rotated at a speed of 1 revolution/5 minutes and a mixture of 95% air and 5% $CO_2$ is passed through the unit at a rate of 100 cc/minute until the cell growth cycle is complete at which time the spent medium and serum is discharged from the propagator, the propagator is then refed with fresh Medium 199 containing 60 ml. 2.8% $NaHCO_3$/L, 2%, G-G-free newborn calf serum and 42.7 ml. of a rubella virus suspension whose titer is $-\log_{10} IND_{50}/0.1$ ml.=3.5, and rotated until the infection process is complete at which time the spent fluids are discharged and the contents of the propagator are washed with Hank's solution. The propagator is then recharged with fresh Medium 199, 60 ml. 2.8% $NaHCO_3$/L and 10% SPGA. When the vaccine has reached the desired concentration the vaccine is harvested.

When the titer of rubella vaccine harvested according to the procedure set forth in this example is compared to the titer of rubella vaccine produced by conventional processes, a significant increase in titer is observed. This increase in titer leads to substantial increases in the yield of vaccine.

EXAMPLE 4

A rotating titanium disc propagator having a stack of 50 discs, each having a plate diameter of 6 inches, an internal tank diameter of 7¼ inches, a distance of five-eighths inch between the edge of the plates and the tank wall and a plate diameter to internal tank diameter ratio of 0.83 is charged with a mixture of Eagle's Basel Medium and tryptose phosphate broth with 5% fetal calf serum and $3 \times 10^9$ cells from trypsinized 12 day duck embryos and $3.6 \times 10^6$ PFU Marek THV. The charged propagator is held in the vertical position at a temperature of 37°C. and plating is effected. The propagator is then positioned so that the plane of the disc is in the vertical axis and a portion of the medium and serum is discharged until the unit is about half full. The discs are then rotated at a speed of 1 revolution/8 minutes and air or a mixture of 95% air and 5% $CO_2$ is passed through the propagator at a flow rate of 100 cc/minute. The pH is adjusted from time to time with 7.5% $NaHCO_3$ so that it remains within the limits of pH 6.8-7.4. Also glucose is added to the system periodically so that at no time should the glucose concentration go outside the limits of 15-100 mg./100 ml. On the sixth day after plating the spent medium is discharged and 6 liters of KCL/trypsin is transferred into the propagator. The plates are then rotated through the trypsin solution at a speed of about 20 revolutions per minute for 5 minutes. The cell suspension is discharged from the propagator and fetal calf serum is added until a final concentration of 7.5% fetal calf serum is obtained. The suspension is then centrifuged for 10 minutes. The contents are then resuspended in 15% fetal calf serum.

When the vaccine is prepared by this method, in the described equipment a substantial increase in titer is obtained when compared with the titer obtained when conventional equipment and procedures are used. This increase in titer leads to greatly increased yields of vaccine.

EXAMPLE 5

A rotating titanium disc propagator having a stack of 50 discs, each having a plate diameter of 6 inches, an internal tank diameter of 7¼ inches, a distance of five-eighths inch between the edge of the plates and the tank wall and a plate diameter to internal tank diameter ratio of 0.83, is charged with a mixture of $300 \times 10^6$ WI-38 cells in Medium EBME containing 10% fetal calf serum and 10 ml. of glutamine/L. The propagator and its contents are then held with the plane of the plates in the horizontal axis at 37°C. until plating has been achieved. The propagator is then positioned so that the plane of the discs is in the vertical axis and a portion of the medium and serum is discharged until the unit is about half full. The discs are then rotated at a speed of 1 revolution/5 minutes and air or a mixture of 5% $CO_2$ and 95% air is passed through the unit at a rate of 100 cc/minute. Twenty-four hours later the medium is discharged from the machine and the unit is refilled with an equal volume of fresh Medium EBME containing 5% fetal calf serum and 10 ml. glutamine/L. After a further 48 hours in the rotating and gassing mode, the unit is harvested. For this operation the unit is voided of spent medium and is then half filled with a solution containing trypsin. The plates are rotated through the trypsin solution at a speed of 20 revolutions per minute for 5 minutes. The cell suspension is discharged from the propagator and fetal calf serum is added until a final concentration of 7.5% fetal calf serum is obtained. The suspension is then centrifuged for 10 minutes to pellitize the cells and the cells are resuspended in Medium 199, 15% fetal calf serum and 45 ml. of 2.8% $NaHCO_3$/L.

When WI-38 cells are prepared by this method in the described equipment, they are prepared with great efficiency and economy when compared to cells produced using conventional procedures and equipment.

EXAMPLE 6

A rotating disc propagator having a stack of 50 discs, each having a plate diameter of 6 inches, an internal tank diameter of 7¼ inches, a distance of five-eighths inch between the edge of the plates and the tank wall and a plate diameter to internal tank diameter ratio of 0.83, is charged with a mixture of 3.0 billion trypsinized chick embryo cells, Medium 199, 45 ml. 2.8% $NaHCO_3$/L and 5% fetal calf serum. The propagator is held in the vertical position at a temperature of 37°C. and plating is effected. After 3 hours the fluid in the propagator is discharged and a further 3.0 billion trypsinized chick embryo cells are added to it and after mixing the fresh suspension is transferred back into the propagator which is held in the opposite vertical position to the first planting at a temperature of 37°C. in order to effect plating on the second side of the discs. When this has been accomplished, the propagator is positioned so that the plane of the discs is in the vertical axis and a portion of the medium and serum is discharged until the unit is about half full. The discs are then rotated at a speed of 1 revolution in 5 minutes and air or a mixture of 5% $CO_2$ and 95% air is passed through the propagator at a rate of 100 cc/min. When the cells have reached the confluent state and the growth has ceased, the cells may be harvested.

The medium in the propagator is discharged and the propagator is filled up to the half way mark with a solution containing trypsin. The plates are rotated through the trypsin solution at a speed of 20 revolutions per minute for 5 minutes. The cell suspension is discharged from the propagator and fetal calf serum is added until a final concentration of 7.5% fetal calf serum is obtained. The suspension is then centrifuged for 10 minutes to pellitize the cells and the cells are resuspended in Medium 199, 15% fetal calf serum and 45 ml. of 2.8% NaHCO₃/L.

When chick embryo cells are prepared by this method in the described equipment, they are prepared with great efficiency and economy when compared to cells produced using conventional procedures and equipment.

EXAMPLE 7

A rotating disc propagator having a stack of 50 discs, each having a plate diameter of 6 inches, an internal tank diameter of 7¼ inches, a distance of five-eighths inch between the edge of the plates and the tank wall and a plate diameter to internal tank diameter ratio of 0.83, is charged with a mixture of 3.0 billion trypsinized duck embryo cells, Medium 199 FlO 5% fetal calf serum, 30 ml. 2.8% NaHCO₃/L. The propagator is held in the vertical position at a temperature of 37°C. and plating is effected. After 3 hours the fluid in the propagator is discharged and a further 3.0 billion trypsinized duck embryo cells are added to it and after mixing the fresh suspension is transferred back into the propagator which is held in the opposite vertical position to the first planting at a temperature of 37°C. in order to effect plating on the second side of the discs. When this has been accomplished, the propagator is positioned so that the plane of the discs is in the vertical axis and a portion of the medium and serum is discharged until the unit is about half full. The discs are then rotated at a speed of 1 revolution in 5 minutes and air or a mixture of 5% $CO_2$ and 95% air is passed through the propagator at a rate of 100 cc/min. When the cells have reached the confluent state and the growth has ceased, the cells may be harvested.

The medium in the propagator is discharged and the propagator is filled up to the half way mark with a solution containing trypsin. The plates are rotated through the trypsin solution at a speed of 20 revolutions per minute for 5 minutes. The cell suspension is discharged from the propagator and fetal calf serum is added until a final concentration of 7.5% fetal calf serum is obtained. The suspension is then centrifuged for 10 minutes to pellitize the cells and the cells are resuspended in Medium 199 FlO 5% fetal calf serum, 30 ml. 2.8% NaHCO₃/L.

When duck embryo cells are prepared by this method in the described equipment, they are prepared with great efficiency and economy when compared to cells produced using conventional procedures and equipment.

The following examples (8–13) illustrate the advantages obtained in the production of cells and vaccines utilizing the multiplate propagator which contains the critical dimensions as compared with the prior art Biotec device.

Examples 8 and 9 relate to the production of mumps virus. The studies were run under identical conditions in all respects with the exception that the process set forth in Example 8 relates to the production of mumps virus utilizing a multiplate propagator possessing the critical dimensions of the invention whereas Example 9 is directed to the prior art Biotec device. In both Examples 8 and 9 the maximum titer obtained during the production of the mumps vaccine is indicated.

Examples 10 and 11 relate to the production of measles virus. The studies were run under identical conditions in all respects with the exception that the process set forth in Example 10 relates to the production of measles virus utilizing a multiple propagator possessing the critical dimensions of the invention whereas Example 11 is directed to the prior art Biotec device. In both Examples 10 and 11 the maximum titer obtained during the production of the measles vaccine are indicated.

Examples 12 and 13 relate to the production of chick embryo cells. The studies were run under identical conditions in all respect with the exception that the process set forth in Example 12 utilizes the apparatus of the present invention whereas Example 13 is directed to the prior art Biotec device; in addition 10% fetal calf serum was employed in Example 12 and 5% fetal calf serum was employed in Example 13. In both Examples 12 and 13, the cell yield obtained on day 3 post-planting is indicated.

EXAMPLE 8

A rotating titanium disc propagator having a stack of 50 discs, each having a plate diameter of 6 inches, an internal tank diameter of 7¼ inches, a distance of five-eighths inch between the edge of the plates and the tank wall, a plate diameter to internal tank diameter ratio of 0.83 and a plate surface area to tank volume ratio of 1.9 cm.²/ml. is charged to the tank's capacity of 4.7 l. with a mixture of 1.5 billion trypsinized chick embryo cells distributed in Medium 0 containing 10% fetal calf serum, wherein Medium 0 consists of:

| Medium O | | |
|---|---|---|
| Medium 199 10X Concentrate | 100 | ml. |
| Solution D-G-P | 1 | ml. |
| 2.8% Sodium Bicarbonate Solution | 45 | ml. |
| 2% Phenol Red Solution | 0.5 | ml. |
| Filtered Distilled Water, q.s. | 1000 | ml. |

The propagator is held in the vertical position at a temperature of 37°C. for 3 hours and plating is effected on one side of the plates. The propagator is then positioned in a horizontal position, drained and recharged to capacity with another 1.5 billion chick embryo cells distributed in Medium 0 and 10% fetal calf serum. The propagator is rotated through 90° so that the second surface of the plates is planted with cells. The plating of the second surface is allowed to proceed for 14 hours. The propagator is then positioned so that the plane of the discs is in the vertical axis and a portion of the medium and serum is discharged until the unit is half full or slightly more than half full. The discs are then rotated at a speed of 1 revolution/5 minutes and a mixture of 95% air and 5% $CO_2$ is passed through the unit at a rate of 100 cc/minute until the cell growth cycle has been completed at which time the spent medium and serum is discharged from the propagator and the propagator is washed with Hank's solution and charged with a seeding medium consisting of fresh Medium 0 with an additional 15 ml. per liter of 2.8% sodium bicarbonate solution with 25% SPGA and 1 ml. of a suspension of mumps virus which has a $-\log_{10}$ $TCID_{50}/0.1$ ml. of 3.6 wherein, SPGA has the following composition:

| SPGA | | |
|---|---|---|
| sucrose | 74.62 | g. |
| monopotassium phosphate | 0.45 | g. |

-continued
SPGA

| | | |
|---|---|---|
| di-potassium phosphate | 1.35 | g. |
| 25% solution of human serum albumin | 40 | ml. |
| L-mono sodium glutamate | 0.956 | g. |
| filtered, distilled water, q.s. | 1000 | ml. |

The unit is rotated at a speed of 1 revolution/5 minutes for 4 days at which time the vaccine is harvested.

The titer of mumps vaccine prepared according to the procedure set forth in this example has a maximum $-\log_{10}\text{TCID}_{50}/0.1$ ml. value of 5.8 which is attained on day 4 post-infection.

EXAMPLE 9

Mumps vaccine is produced in the manner identical to that set forth in Example 8 with the exception that a rotating titanium disc propagator having a stack of 50 discs, each having a plate diameter of 6 inches, an internal tank diameter of 6¼ inches, a distance of one-eighth inch between the edge of the plates and the tank wall, a plate diameter to internal tank diameter ratio of 0.96 and a plate surface area to tank volume ratio of 3 cm.$^2$/ml. is employed. The maximum titer value $-\log_{10}\text{TCID}_{50}/0.1$ ml. of 3.1 is obtained on day 7 post-infection.

EXAMPLE 10

A rotating disc propagator having a stack of 50 discs, each having a plate diameter of 6 inches, an internal tank diameter of 7¼ inches, a distance of five-eighths inch between the edge of the plates and the tank wall, a plate diameter to internal tank diameter ratio of 0.83, and a surface area to volume ratio of 1.9 cm.$^2$/ml. is charged to the tank's capacity of 4.7 l. with a mixture of 1.5 billion trypsinized chick embryo cells distributed in Medium 0 containing 10% fetal calf serum. The propagator is held in the vertical position at a temperature of 37°C. for 3 hours and plating is effected. After 3 hours the fluid in the propagator is discharged and a further 1.5 billion trypsinized chick embryo cells is distributed in the discharged fluid by mixing, and the fresh suspension is transferred back into the propagator which is held in the opposite vertical position to the first plating at a temperature of 37°C. for 16 hours. After plating has been completed the propagator is then positioned so that the plane of the discs is in the vertical axis and a portion of the medium and serum is discharged until the unit is about half full. The discs are then rotated at a speed of 1 revolution/5 minutes and a mixture of 95% air and 5% $CO_2$ is passed through the unit at a rate of 100 cc/min. until the cell growth cycle is completed (4 days after planting) at which time the spent medium and serum is discharged from the propagator. The propagator is then refed with fresh Medium 0 with an additional 15 ml. per liter of 2.8 % sodium bicarbonate solution and 2% α-gamma calf serum and 11 ml. of a measles virus suspension which has a $-\log_{10}\text{TCID}_{50}/0.1$ ml. of 3.3 and rotated until the infection process is complete (3 days after seeding) at which time the spent fluids are discharged and the contents of the propagator are washed with Hank's solution. The propagator is then recharged with fresh Medium 0 with an additional 15 ml. per liter of 2.8% sodium bicarbonate solution and 10% SPGA.

SPGA

| | | |
|---|---|---|
| sucrose | 74.62 | g. |
| monopotassium phosphate | 0.45 | g. |
| di-potassium phosphate | 1.35 | g. |
| 25% solution of human serum albumin | 40 | ml. |
| L-mono sodium glutamate | 0.956 | g. |
| filtered, distilled water, q.s. | 1000 | ml. |

After 12 days the vaccine has reached the maximum concentration and the vaccine is harvested.

The maximum titer of measles vaccine prepared according to the procedure set forth in this example has a $-\log_{10}\text{TCID}_{50}/0.1$ ml. of 4.6 which is attained on day 12 post-infection.

EXAMPLE 11

Measles vaccine is produced in the manner identical to that set forth in Example 10 with the exception that a rotating disc propagator having a stack of 50 discs, each having a plate diameter of 6 inches, an internal tank diameter of 6¼ inches, a distance of one-eighth inch between the edge of the plates and the tank wall, a plate diameter to internal tank diameter ratio of 0.96 and a surface area to volume ratio of 3 cm.$^2$/ml. is employed. The maximum titer value $-\log_{10}\text{TCID}_{50}/0.1$ ml. of 2.6 is obtained on day 14 post-infection.

EXAMPLE 12

A rotating disc propagator having a stack of 50 discs, each having a plate diameter of 6 inches, an internal tank diameter of 7¼ inches, a distance of five-eighths inch between the edge of the plates and the tank wall and a plate diameter to internal tank diameter ratio of 0.83, and a surface area to volume ratio of 1.9 cm.$^2$/ml. is charged with a mixture of 3.0 billion trypsinized chick embryo cells, Medium 0, 45 ml. 2.8% $NaHCO_3$/L and 10% fetal calf serum. The propagator is held in the vertical position at a temperature of 37°C. for 3 hours and plating is effected. After 3 hours the fluid in the propagator is discharged and a further 3.0 billion trypsinized chick embryo cells are added to it and after mixing the fresh suspension is transferred back into the propagator which is held in the opposite vertical position to the first planting at a temperature of 37°C. for 14 hours in order to effect plating on the second side of the discs. When this has been accomplished, the propagator is positioned so that the plane of the discs is in the vertical axis and a portion of the medium and serum is discharged until the unit is about half full. The discs are then rotated at a speed of 1 revolution in 5 minutes and a mixture of 5% $CO_2$ and 95% air is passed through the propagator at a rate of 100 cc/min. On the third day after planting, the cells are harvested as follows; the medium in the propagator is discharged and the propagator is filled up to the half way mark with a solution containing trypsin. The plates are rotated through the trypsin solution at a speed of 20 revolutions per minute for 5 minutes. The cell suspension is discharged from the propagator into a bottle containing enough fetal calf serum for a final concentration of 10% fetal calf serum. A sample is withdrawn to determine the total number of cells harvested.

When chick embryo cells are prepared by this method in the described equipment a cell yield of 4.3 × $10^9$ is attained on day 3 post-planting.

EXAMPLE 13

Chick embryo cells are prepared in the manner set forth in Example 12 with the exception that a rotating disc propagator having a stack of 50 discs, each having a plate diameter of 6 inches, an internal tank diameter of 6¼ inches, a distance of one-eighth inch between the edge of the plates and the tank wall and a plate diameter to internal tank diameter ratio of 0.96, and a surface area to volume ratio of 3 cm.$^2$/ml., is employed. In addition, 5% fetal calf serum is utilized in place of 10% fetal calf serum. A cell yield of $1.7 \times 10^9$ is attained on day 3 post-planting.

A comparison of the yield of chick embryo cells in Examples 12 and 13 illustrates that employing the apparatus having the dimensions of the present invention (Example 12) the yield is two times greater than when conventional apparatus is used (Example 13).

What is claimed is:

1. A process for the production of a vaccine wherein the improvement comprises growing a desired virus in a rotating multiplate propagator having a plate diameter to internal tank diameter ratio of from about 0.80 to about 0.90.

2. A process as in claim 1 wherein the ratio is from about 0.82 to about 0.84.

TABLE 1

| Example | Plate/Internal Tank | | Distance Between Edge of Plate and Tank Wall | Plate Surface Area/Tank Volume | Maximum Titer ($-\log_{10}$ TCID$_{50}$/0.1 ml.) | Cell Yield |
|---|---|---|---|---|---|---|
| 8 | Present invention | 0.83 | 5/8" | 1.9 cm.$^2$/ml. | 5.8 | — |
| 9 | prior art | 0.96 | 1/8" | 3 cm.$^2$/ml. | 3.1 | — |
| 10 | present invention | 0.83 | 5/8" | 1.9 cm.$^2$/ml. | 4.6 | — |
| 11 | prior art | 0.96 | 1/8" | 3 cm.$^2$/ml. | 2.6 | — |
| 12 | present invention | 0.83 | 5/8" | 1.9 cm.$^2$/ml. | — | $4.3 \times 10^9$ |
| 13 | prior art | 0.96 | 1/8" | 3 cm.$^2$/ml. | — | $1.7 \times 10^9$ |

Table I summarizes the results of the studies reported in Examples 8–13.

In Example 8 wherein the propagator having the critical dimensions was employed in the production of mumps vaccine, a maximum titer of 5.8 was obtained. In comparison, Example 9 wherein the prior art propagator was utilized, the maximum titer obtained was 3.1. From a consideration of Examples 8 and 9, the distinct and unexpected improvement in the production of mumps vaccine utilizing the propagator of critical dimensions is readily apparent in that yields of vaccine are obtained which are more than 100 times greater than that produced by conventional methods.

In Example 10 wherein the propagator having the critical dimensions was employed in the production of measles vaccine, a maximum titer of 4.6 was obtained. In comparison, Example 11 wherein the prior art propagator was utilized, the maximum titer obtained was 2.6. From a consideration of Examples 10 and 11, the distinct and unexpected improvement in the production of measles vaccine utilizing the propagator of critical dimensions is readily apparent in that yeilds of vaccine are obtained which are 100 times greater than that produced by conventional methods.

3. A process for the production of a vaccine wherein the improvement comprises growing a desired virus in a rotating multiplate propagator having a distance of from about one-half inch to about three-fourths inch between the edge of the plates and the tank wall and having a plate diameter to internal tank diameter ratio of from about 0.80 to about 0.90.

4. A process for the production of a vaccine wherein the improvement comprises growing a desired virus in a multiplate propagator having a surface area to volume ratio of from about 1.7 cm.$^2$/ml. to 2.2 cm.$^2$/ml and having a plate diameter to internal tank diameter ratio of from about 0.80 to about 0.90.

5. A process for the production of a vaccine wherein the improvement comprises growing a desired virus in a rotating multiplate propagator having:
   a. a plate diameter to internal tank diameter of from about 0.80 to 0.90;
   b. a distance of from about one-half inch to about three-fourths inch between the edge of the plates and the tank wall; and
   c. a surface area to volume ratio of from about 1.7 cm.$^2$/ml. to 2.2 cm.$^2$/ml.

* * * * *